United States Patent [19]

Guinn

[11] Patent Number: 4,747,950

[45] Date of Patent: May 31, 1988

[54] METHOD AND APPARATUS FOR CONTROLLED ULTRAFILTRATION DURING HEMODIALYSIS

[75] Inventor: Perry W. Guinn, Gladstone, Oreg.

[73] Assignee: CD Medical, Inc., Miami Lakes, Fla.

[21] Appl. No.: 873,264

[22] Filed: Jun. 6, 1986

Related U.S. Application Data

[63] Continuation of Ser. No. 562,328, Dec. 16, 1983, abandoned.

[51] Int. Cl.⁴ .............................................. B01D 13/00
[52] U.S. Cl. ................................. 210/646; 210/257.2; 210/321.76
[58] Field of Search ................... 210/86, 96.2, 321.3, 210/257.2, 929, 646, 321.76

[56] References Cited

U.S. PATENT DOCUMENTS

| | | | |
|---|---|---|---|
| 3,757,947 | 9/1973 | Wakefield et al. | 210/86 |
| 4,178,240 | 12/1979 | Pinkerton | 210/929 X |
| 4,372,846 | 2/1983 | Yamagami et al. | 210/929 X |
| 4,486,303 | 12/1984 | Brous | 210/321.3 X |

FOREIGN PATENT DOCUMENTS 2397197 11/1978 France .................................. 210/927
2457694 1/1981 France .................................. 210/929

Primary Examiner—Frank Spear

[57] ABSTRACT

A method of hemodialytic ultrafiltration in a device utilizing a dialysate flow path, a hemodialyzer, a first receptacle and a second receptacle comprises supplying fresh dialysate to the first receptacle. Spent dialysate is withdrawn from the second receptacle at substantially the same rate fresh dialysate is supplied to the first receptacle. This method includes variably withdrawing fresh dialysate from the first receptacle and supplying same to the hemodialyzer, and variable withdrawing spent dialysate from the hemodialyzer and delivering same to the second receptacle. The dialysate levels in the receptacles are maintained at relatively constant, pre-determined levels. Further, this method includes withdrawing a controlled amount of dialysate from the dialysate flow path between and including the receptacles to thereby effect a withdrawal of ultrafiltrate from the patient's blood into the flow path to substantially balance the amount of dialysate withdrawn therefrom.

A hemodialysis ultrafiltration apparatus carries out the method substantially as described above.

21 Claims, 3 Drawing Sheets

METHOD AND APPARATUS FOR CONTROLLED ULTRAFILTRATION DURING HEMODIALYSIS

CROSS REFERENCE TO RELATED APPLICATION

This is a continuation of application Ser. No. 562,328, filed Dec. 16, 1983, now abandoned.

BACKGROUND OF THE INVENTION

1. Field of the Invention

The present invention relates to a volumetric ultrafiltration system and its method of use, a volumetric infusion system and its method of use, and more particularly, concerns a method and apparatus for controlling ultrafiltration during hemodialysis.

2. Description of the Prior Art

Ultrafiltration is the procedure during hemodialysis wherein excess water is removed from the blood. It is well-known to achieve satisfactory ultrafiltration by maintaining the dialysate pressure within the dialyzer lower than that of the blood pressure. During this procedure, while excess water in the blood is removable, the rate of ultrafiltration is a critical factor, since rapid removal of water from the blood may traumatically affect the patient. Various solutions to the control of the rate of ultrafiltration have been proposed, such as those described in U.S. Pat. Nos. 3,939,069; 4,209,391; and 4,267,041.

U.S. Pat. No. 4,209,391, in particular, achieves ultrafiltration control by utilization of a volumetric system relying upon a principle of volume conservation. In the patented apparatus, a known and equal quantity of fluid is moved into and out of the dialyzer by two matched positive displacement pumps. As dialysate is moved to the dialyzer, a third pump extracts the programmed amount of dialysate from the fresh dialysate supply. The spent dialysate line demands a fixed quantity of fluid and the difference that is drawn off the fresh dialysate supply is made up by the ultrafiltrate drawn across the dialyzer membrane.

In U.S. Pat. No. 3,939,069, a constant volume closed system of hemodialysis is described. A fraction of the dialysis liquid is pumped from the system at a predetermined rate in order to ensure predetermined ultrafiltration flow during a hemodialysis session. The remainder of the dialysis liquid is kept at a constant temperature and is regenerated.

U.S Pat. No. 4,267,041 discloses an apparatus including a plurality of storage containers for the dialysis liquid. These containers are connected in parallel flow arrangement to each other by groups of valves which are controlled by an automatic timer mechanism so that the containers may be operatively connected to the circulatory system in a timed sequence. A branching pump is provided for withdrawing dialysis liquid from the system to control the ultrafiltration in connection with the hemodialysis treatment.

While the inventions described in the foregoing patents represent improvements in controlling ultrafiltration during hemodialysis, further improvements are still being sought. In particular, the desiderata to which such further improvements are directed include simplicity, accuracy and flexibility of use on a variety of dialysis equipment. It is toward the achievement of these desired features and other improved characteristics that the present invention is directed.

SUMMARY OF THE INVENTION

The method of hemodialytic ultrafiltration in a device utilizing a dialysate flow path, a hemodialyzer, a first receptacle and a second receptacle comprises supplying fresh dialysate to the first receptacle. Spent dialysate is withdrawn from the second receptacle at a rate substantially equivalent to the rate fresh dialysate is supplied to the first receptacle. Fresh dialysate is variably withdrawn from the first receptacle and is supplied to the hemodialyzer. Spent dialysate is variably withdrawn from the hemodialyzer and is delivered to the second receptacle. This method includes maintaining the dialysate levels in the receptacles at substantially equivalent, predetermined levels. A controlled amount of dialysate is withdrawn from either of the receptacles to thereby effect a withdrawal of ultrafiltrate from the patient's blood into the flow path to substantially balance the amount of dialysate withdrawn therefrom. Blood from the patient is supplied to the hemodialyser and is also removed therefrom.

In a preferred embodiment of this aspect of the invention, fresh dialysate is first supplied to a reservoir. Fresh dialysate is withdrawn from the reservoir and delivered to the first receptacle and then the hemodialyzer at a controlled rate. This method includes sensing the volume of fresh dialysate in the first receptacle and maintaining it at a relatively constant, predetermined level. Further, the volume of spent dialysate in the second receptacle is sensed and this volume is maintained at a relatively constant, predetermined level. Withdrawing dialysate from either of the receptacles causes a system response which exerts a negative pressure in the dialysate section of the hemodialyzer to effect the withdrawal of ultrafiltrate from the patient's blood into the dialysate flow path.

In another aspect of the present invention, a hemodialysis ultrafiltration apparatus comprises a dialysate flow path. Included in this flow path is a hemodialyzer, a first receptacle and a second receptacle. First means supplies fresh dialysate to the first receptacle and withdraws spent dialysate from the second receptacle at substantially equivalent, fixed rates. Second means variably withdraws fresh dialysate from the first receptacle and supplies it to the hemodialyzer and also variably withdraws spent dialysate from the hemodialyzer and delivers it to the second receptacle. Control means associated with the receptacles and the first and second means, mentioned above, maintains the dialysate levels in the receptacles at substantially constant, predetermined levels. Ultrafiltrate removal means withdraws a controlled amount of dialysate from either of the receptacles to thereby effect a withdrawal of ultrafiltrate from the patient's blood into the flow path to substantially balance the amount of dialysate withdrawn therefrom.

A further aspect of the present invention includes a method and apparatus for hemodialytic infusion. This method and apparatus are substantially the same as the method and apparatus for ultrafiltration, except that the ultrafiltrate removal step and means, respectively, is reversed in direction. This reversal in conjunction with infusate delivery means supplies a controlled amount of infusate to the fresh dialysate in the first receptacle. This causes an infusion of infusate into the patient's blood from the flow path to substantially balance the amount of infusate supplied thereto.

In accordance with the principles of the present invention, a volumetric ultrafiltration system for hemodialysis is provided which is simple and straightforward in structure, design and use, operates accurately and has the flexibility to be used on a variety of dialysis machines. Further, the present invention operates independently of the dialysate proportioning system found in typical dialysis machines. Accuracy of the present invention is not affected by air which is one critical source of error in presently known and available ultrafiltration devices. Any errors in the present invention are limited to total compliance of the dialyzer, tubing and volume of liquid in the receptacles. In addition, the present invention may be operated at atmospheric pressure, which is preferable, or may be operated at a preselected pressure which is different from atmospheric pressure. The present invention is readily calibrated so that mass balance of the fresh dialysate and spent dialysate is achieved during operation of the equipment. Once such mass balance occurs, ultrafiltration is expeditiously performed. Furthermore, the positioning of the ultrafiltration removal means is not critical and may be located to withdraw dialysate from either of the receptacles, or the dialysate flow path between the receptacles, containing fresh dialysate or spent dialysate. As pointed out above, the present invention may also be employed to accurately infuse liquid into a patient preferably by reversing the flow of the ultrafiltrate removal pump or similar means.

DETAILED DESCRIPTION

Figure 1:
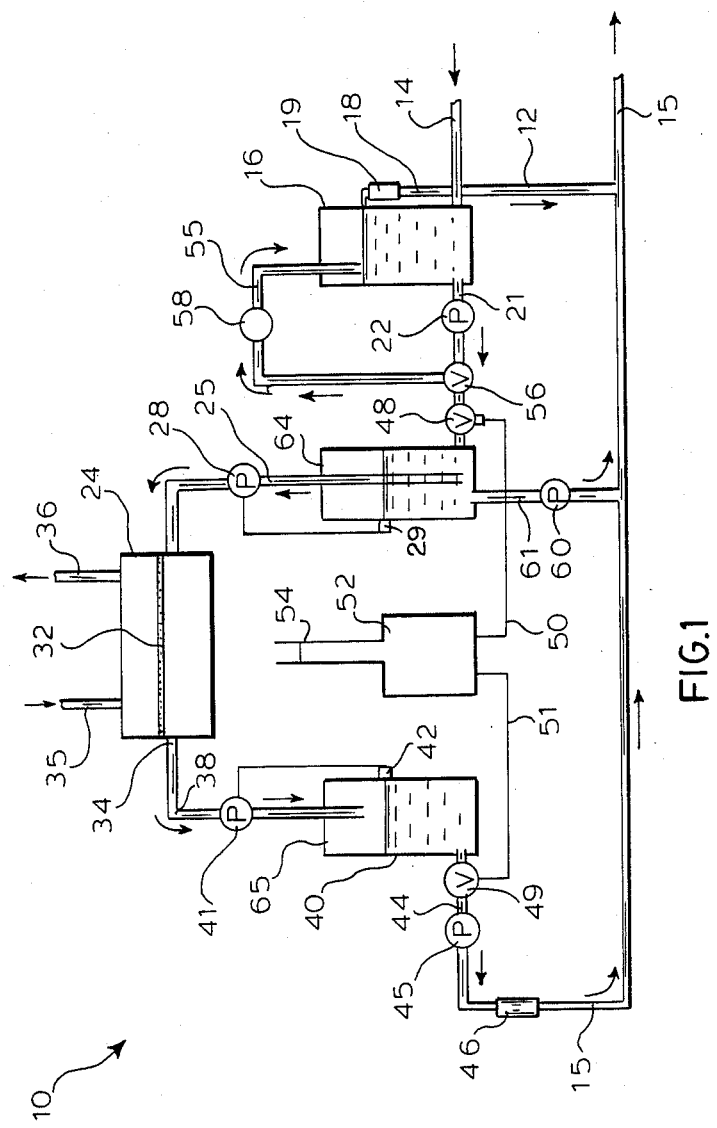
FIG. 1 is a schematic representation of a flow diagram illustrating the preferred apparatus of the present invention for controlling ultrafiltration during hemodialysis.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Turning to the drawings, and FIG. 1 in particular, there is illustrated a schematic representation of the preferred apparatus 10 for controlling ultrafiltration during hemodialysis. It is understood that only the major components of the present invention are represented herein, with the minor components being well within the purview of one skilled in the art to ascertain. Apparatus 10 comprises a continuous loop or circuit flow path 12 for dialysate originating with a fresh dialysate supply line 14 and terminating in a spent dialysate removal line 15. Supply line 14 is connectable to the host dialysis machine so that fresh dialysate may be delivered to apparatus 10. Similarly, removal line 15 is connectable to the same host dialysis machine and provides a mechanism for draining spent dialysate from the apparatus herein described. Thus, all fresh dialysate enters flow path 12 through supply line 14 while all spent dialysate leaves the closed loop flow path by being drained from removal line 15.

Connected immediately to supply 14 is a reservoir 16 which holds a quantity of fresh dialysate which is delivered thereto. An overflow line 18 is provided in case the level of fresh dialysate inside the reservoir exceeds a pre-determined level. This overflow line 18 is connected to removal line 15 so that excess dialysate is readily drained from the flow path. An air vent 19 is included in overflow line 18 near the interface with the first receptacle to control the pressures influencing the operation of the pumps to be described hereinafter.

A first receptacle 20 is included in the continuous loop flow path and is in fluid communication with reservoir 16 by virtue of flow line 21. A first metering pump 22, in flow line 21, is provided to withdraw fresh dialysate from the reservoir and deliver it to the first receptacle. Pump 22 is intended to operate at a fixed rate of speed for delivering fresh dialysate at a pre-determined, controlled rate to the receptacle. From the first receptacle, the flow path extends to the dialysate section of a hemodialyzer 24 by virtue of flow line 25 which provides fluid communication between the first receptacle and an inlet dialysate port 26 of the hemodialyzer. In order to withdraw fresh dialysate from the first receptacle and deliver it to the hemodialyzer, another pump 28 is provided. Pump 28 is preferably a variable flow pump which is controllable to adjust the rate of flow of the fresh dialysate toward the hemodialyzer. The reason that variable rates of fresh dialysate delivery are required is related to the level or volume of fresh dialysate in the first receptacle. As part of the mass balance between fresh dialysate supply to the hemodialyzer and spent dialysate coming therefrom, the level of fresh dialysate in the first receptacle should be maintained relatively constant, preferably at a predetermined level. A liquid sensing device 29 is included in first receptacle 20 to detect the level or volume of liquid contained therein. Sensing device 29 is preferably electrically connected to pump 28 so that the flow from pump 28 can be varied as a function of the level of liquid inside the first receptacle. For instance, if the level of liquid is lower than a pre-determined level, the flow from pump 28 would be decreased whereby the level of liquid in the first receptacle would increase; conversely, if the level of liquid is higher than the pre-determined level, sensing device 29 would control the flow from pump 28 to increase the flow to readjust the level downward toward the pre-determined level.

Hemodialyzer 24 may be any of the well-known dialyzers useful for hemodialysis and including a membrane 32 therein adapted to remove waste materials and ultrafiltrate from the blood. Fresh dialysate enters the hemodialyzer through dialysate inlet port 26, and after collecting waste materials and ultrafiltrate from the blood, spent dialysate exits the hemodialyzer through dialysate outlet port 34. The hemodialyzer, of course, includes a blood inlet port 35 through which blood from a hemodialysis patient enters. A blood outlet port 36 is provided on the hemodialyzer to return blood, from which waste materials and ultrafiltrate have been removed, to the patient.

Spent dialysate is withdrawn from hemodialyzer 24 through flow line 38 and is delivered into a second receptacle 40. Facilitating this withdrawal of spent dialysate is a second variable rate pump 41 which is provided in flow line 39. Pump 41 is preferably, but not necessarily, similar to pump 28, and has its flow controlled by virtue of a liquid sensing device 42 which, once again, is similar to sensing device 29. Sensing device 42, however, senses the level or volume of spent dialysate inside receptacle 40 and is electrically connected to pump 41 to adjust its flow during in-line operation to assure that the level of spent dialysate in the second receptacle is maintained at a relatively constant, pre-determined level. Preferably, the pre-determined levels to be sensed in both receptacles are tightly controlled, thereby contributing to mass balance of dialysate entering and leaving the hemodialyzer.

Spent dialysate is withdrawn from second receptacle 40 through a flow line 44 which is in fluid communication with spent dialysate removal line 15. A second, preferably, but not necessarily, fixed rate pump 45 is positioned in flow line 44 to withdraw spent dialysate from the second receptacle at substantially the same controlled rate that pump 22 withdraws fresh dialysate from the reservoir for delivery to the first receptacle. An air vent 46, similar to air vent 19, is included in removal line 15 near the output side of pump 45 for regulating pressures influencing the operation of the pumps. By balancing the liquid output of pump 22 with the liquid intake of pump 45, mass balance of dialysate entering the hemodialyzer and leaving the hemodialyzer will occur. It is appreciated that if the flow of fresh dialysate into the hemodialyzer balances the flow of spent dialysate leaving the hemodialyzer, the patient will not experience ultrafiltration. Accordingly, the mechanism to control ultrafiltration, as hereinafter described, can be very accurately and straightforwardly accomplished. Matching the output of pump 22 with the intake of fixed rate pump 45, however, is important to effectuate the straight-forward control of ultrafiltration.

Calibration of pumps 22 and 45 may be accomplished in a number of ways. One preferable technique is illustrated in FIG. 1. Receptacles 20 and 40 are by-passed by closing valves 48 and 49 in flow lines 21 and 44, respectively. Closing these valves opens shunt lines 50 and 51 connected to a calibration chamber 52. To calibrate pumps 22 and 45, it is preferred to operate pump 22 at a slightly greater speed than pump 45. A calibration bleed-off line 55 is connected at one end to flow line 21 at the output side of pump 22 and is connected on the other end to reservoir 16. During calibration, a valve 56 is opened while pump 22 is operating at a greater speed than pump 45, and while shunt lines 50 and 51 are opened. Calibration is achieved by bleeding-off excess fresh dialysate through port 58 until the level of liquid in sight tube 54 remains at a constant level. Valves 48, 49 and 56 are then closed with the assurance that the output of pump 22 substantially balances the intake of pump 45.

It is appreciated that the respective pumps may be balanced in other ways, including the use of the same motor to operate both pumps. Moreover, instead of bleeding excess fresh dialysate through bleed-off line 55, a variable restriction may be placed in the dialysate flow path to restrict the flow of fresh or spent dialysate flow therethrough, particularly when pump 22 operates at a higher speed than pump 45. Once mass balance of dialysate has occurred, ultrafiltration is achieved by withdrawing a controlled amount of dialysate from either of the receptacles. A pump is preferably relied upon for such removal, and its position in the closed circuit dialysate flow path is not critical as long as it is placed between the output side of pump 22 and the intake side of pump 45. In the embodiment of FIG. 1, ultrafiltrate removal pump 60 is positioned in a flow line 61 extending between first receptacle 20 and spent dialysate removal line 15. By withdrawing a controlled amount of fresh dialysate from receptacle 20, the equilibrium of the fresh and spent dialysate is changed thereby causing a withdrawal of ultrafiltrate from the patient's blood. Thus, the operation of ultrafiltrate pump 60 can be controlled and programmed to withdraw metered quantities of dialysate from the flow path causing ultrafiltrate to be removed from the patient's blood in known and calculable amounts. Operation of the apparatus of FIG. 1 will now be described.

Preferably, apparatus 10 operates at atmospheric pressure. To that end, air vents 64 and 65 in receptacles 20 and 40, respectively are provided. Fresh dialysate supply line 14 is appropriately connected to the host dialysis machine (not shown) and spent dialysate removal line 15 is also appropriately connected to the host dialysis machine. Fresh dialysate, delivered to reservoir 16 from the host machine, has been premixed, preheated and degassed as necessary. Pumps 22 and 45 have been calibrated, such as described above, so that the output of pump 22 balances the intake of pump 45. Accordingly, pump 22 withdraws a controlled amount of fresh dialysate from the reservoir, which typically may be at the rate of 500 ml/min, and delivers the fresh dialysate to receptacle 20. Pump 28 withdraws fresh dialysate from receptacle 20 at substantially the same rate that the fresh dialysate is delivered to the first receptacle. The level of fresh dialysate in receptacle 20 is held substantially constant in accordance with the level or volume sensing device 29 as described above which controls the flow rate at which pump 28 operates. When dialysate has passed through hemodialyzer 24, pump 41 withdraws the spent dialysate therefrom and delivers same to receptacle 40. Similarly, level or volume sensing device 42 adjusts the flow from pump 41 to maintain a relatively constant, pre-determined level of spent dialysate in receptacle 40. Spent dialysate is removed from the hemodialyzer also at substantially the same rate that fresh dialysate is delivered thereto. From receptacle 40, spent dialysate is withdrawn by virtue of pump 45 whereupon the spent dialysate enters removal line 15 so that it may be drained from the system. Once again, pump 45 withdraws spent dialysate at substantially the same rate that fresh dialysate is withdrawn by pump 22 from reservoir 16. If pumps 22 and 45 have been matched so that the output of pump 22 substantially matches the intake of pump 45, mass balance of dialysate will be achieved.

When mass balance has occurred, ultrafiltrate removal pump 60 is activated to withdraw a controlled amount of dialysate from receptacle 20. This amount may vary according to the needs and condition of the patient, and may typically range between zero and 300 ml/min. By withdrawing dialysate from the first receptacle, an imbalance in the pre-established equilibrium occurs which causes pumps 28 and 41 to increase or decrease flow rates to once again seek the equilibrium of the pre-determined levels of dialysate in the respective receptacles. While this is occurring, a negative or positive pressure is exerted in the dialysate section of the hemodialyzer to effect a withdrawal of ultrafiltrate from the patient's blood across membrane 32. This ultrafiltrate enters the dialysate flow path to substantially balance the amount of dialysate withdrawn therefrom. Thus, the amount of ultrafiltrate removed from the patient's blood matches the amount of dialysate withdrawn from either of the receptacles. It can be seen that this mechanism of controlling ultrafiltration during hemodialysis is simply constructed, straight-forward in use and performs accurately, particularly since accuracy is not affected by air in the system.

While the embodiment of FIG. 1 has been described as preferably operating at atmospheric pressure, it is not limited to operation at that pressure. For example, air vents 64 and 65 in receptacles 20 and 40, respectively, may be closed to provide a substantially air-tight closed circuit section between pump 22 and pump 45. In this configuration, the ultrafiltration apparatus of FIG. 1 may be operated at a chosen pressure within the design capabilities of the system. If other than atmospheric pressure operation is selected, however, the pressures inside receptacles 20 and 40 should be tightly controlled. An air trap (not shown) should also be included in the line between pump 41 and receptacle 40. Further, instead of relying on the levels or volumes of dialysate in the respective receptacles for producing mass balance, sensing devices 29 and 42 could be selected to sense pressures inside the respective receptacles. Use of pressure sensors would then be compatible with operation of the apparatus at a pressure other than atmospheric pressure.

There are also other techniques for producing mass balance of the fresh and spent dialysate besides the preferable variable rate pumps as described in conjunction with FIG. 1. For instance, instead of varying the flow rates of pumps 28 and 41 to maintain the levels of dialysate in the receptacles, the speed of the pumps may be held constant. Flow control may be established by way of variable recirculating loops (not shown) which may contain control valves which are regulated by the levels of liquid in the respective receptacles. Other techniques are also within the purview of the present invention.

Figure 2:
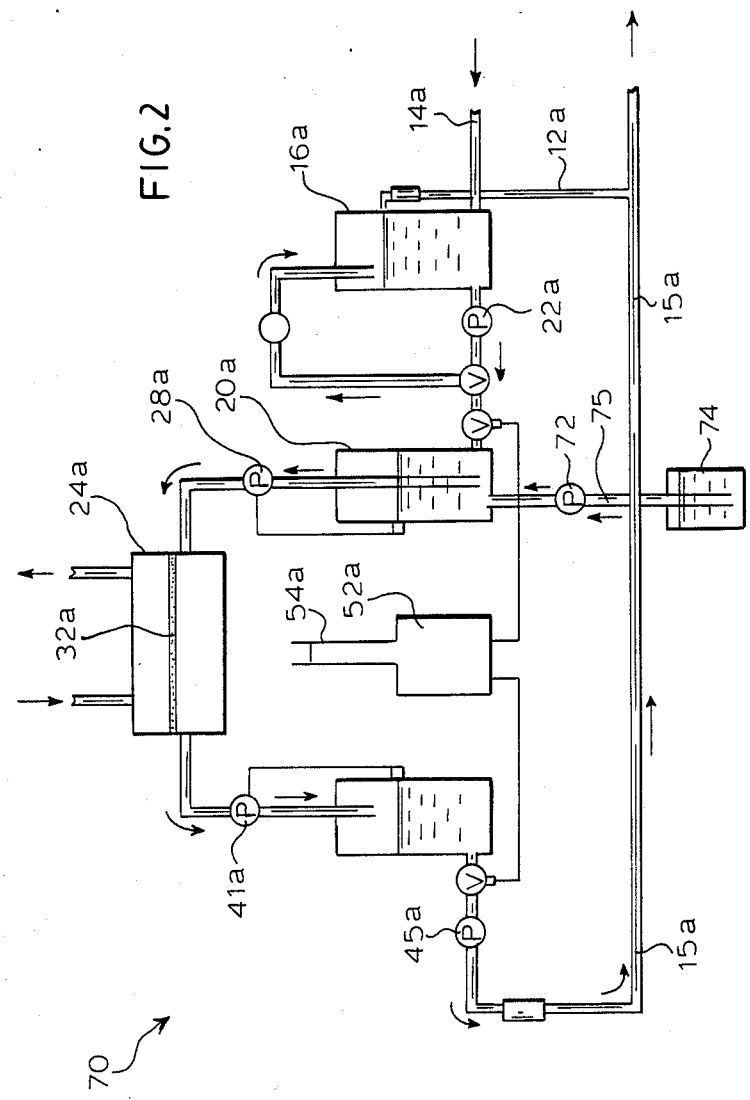
FIG. 2 is a schematic representation of a flow diagram illustrating the preferred apparatus of the present invention for controlling infusion during hemodialysis.

Moreover, whereas the embodiment of FIG. 1 has been described in conjunction with controlling ultrafiltration during hemodialysis, the present invention is also suitable for delivering liquid infusate in controlled amounts to the patient during hemodialysis. FIG. 2 illustrates the use of the present invention for such infusion purposes. It can be seen that in all respects, except those items mentioned below, infusion apparatus 70 is the same as ultrafiltration apparatus 10 as illustrated in FIG. 1. Accordingly, the elements or components of apparatus 70 which similarly correspond to elements of apparatus 10 have been designated with the same numerals as found in apparatus 10 followed by the suffix "a." The modification of apparatus 10 lies essentially in the arrangement of infusate delivery pump 72. It can be seen that pump 72 is not connected to removal line 15a in the same fashion as ultrafiltrate pump 60 is connected to removal line 15 as described above. On the other hand, an infusate container 74 for holding infusate is provided and a flow line 75 is in fluid communication between container 74 and first receptacle 20a. Infusate delivery pump 72, which operates in reverse fashion from ultrafiltrate removal pump 60, withdraws infusate from container 74 in a controlled amount and supplies this infusate to the fresh dialysate in first receptacle 20a. Once mass balance between the fresh and spent dialysate has been achieved, addition of the liquid infusate into receptacle 20a will change the equilibrium characteristics. In this case, however, a positive pressure is exerted in the dialysate section of hemodialyzer 24a to effect an infusion of infusate across membrane 32 and into the patient's blood. The amount of infusate delivered to the patient balances the amount of infusate supplied into the dialysate flow path. Therefore, by slightly modifying the ultrafiltration apparatus of FIG. 1, a mechanism is provided for infusing accurate and controlled amounts of liquid into the patient.

It is understood that there may be many modifications to the themes described above which fall within the purview of the present invention. Without limiting the modifications to the following, one such alternative includes replacing variable speed pump 28 with a control valve. While this approach may be less expensive than the use of the variable speed pump, some sacrifice in operation is necessary. Specifically, if a control valve is used, zero ultrafiltration may not be possible to achieve. However, this may not be a significant sacrifice because most dialysis procedures today are performed with this limitation.

Another alternative includes deleting both preferably fixed rate pumps 22 and 45 and replacing them with metering valves or flow restrictors. In this approach, judicious rearrangement of the receptacles will permit gravity to perform the pumping operation that pumps 22 and 45 had assumed.

In a further alternative, reservoir 16 may function without overflow line 18 connected to removal line 15. Instead, a control valve, upstream of the reservoir, can be used to regulate the amount of fresh dialysate within the reservoir. This control valve would operate in similar fashion to sensing devices 29 and 42.

Figure 3:
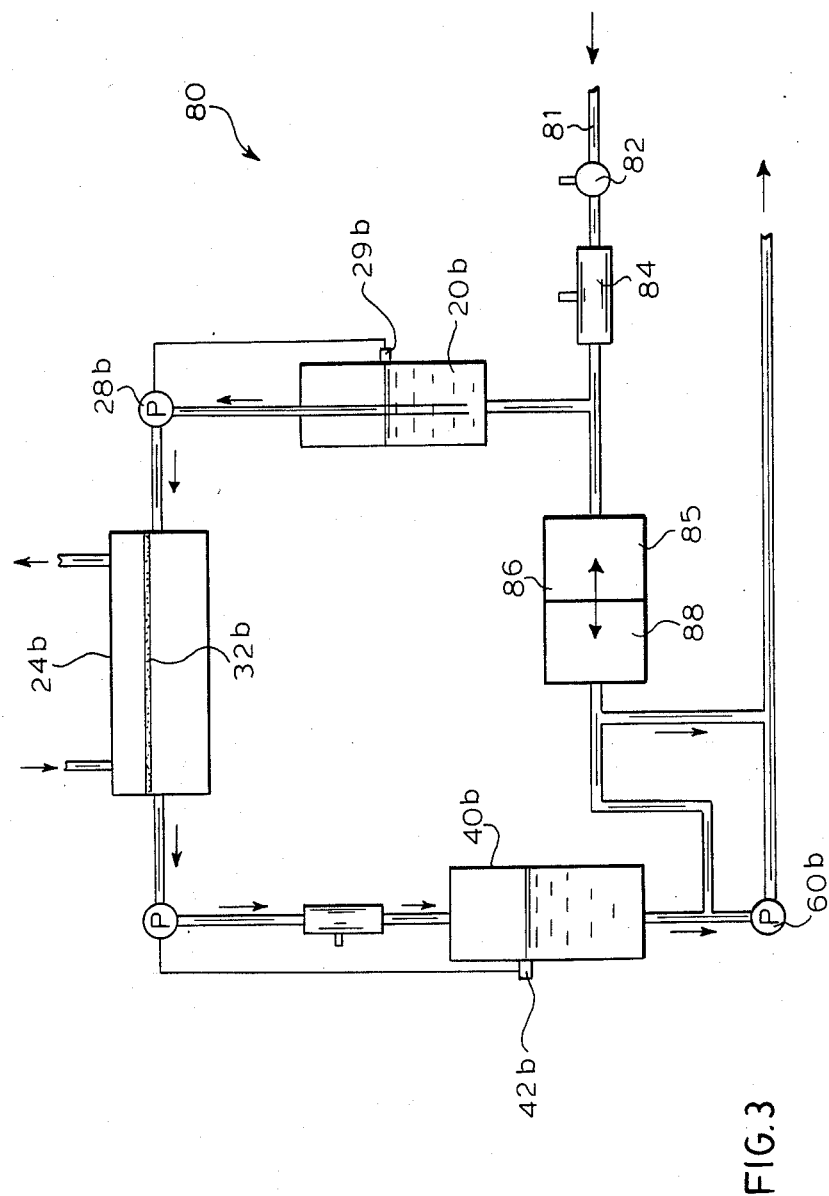
FIG. 3 is a schematic representation of a flow diagram illustrating an alternative embodiment of an apparatus of the present invention for controlling ultrafiltration during hemodialysis.

Instead of relying on the two preferably fixed rate pumps 22 and 45, they could be replaced with a double acting piston or diaphragm, such as illustrated in FIG. 3. In this embodiment, which in many respects is similar to the configuration of FIG. 1, there is, however, no reservoir. Fresh dialysate from the host machine (not shown) is delivered to the ultrafiltration apparatus 80 through flow line 81. A pressure regulator 82 and air trap 84 are provided in flow line 81 to regulate the flow of fresh dialysate. Double acting piston 85, similar to that described in U.S. Pat. No. 4,209,391, includes two chambers, 86 and 88, respectively. Chamber 86 regulates the delivery of fresh dialysate into first receptacle 20b, while chamber 88 regulates the withdrawal of spent dialysate from second receptacle 40b. The remaining elements of this alternative embodiment are similar to those described above in conjunction with FIG. 1. Ultrafiltration pump 60b may be driven by the action of variable speed pump 41b which may also drive the inlet of chamber 88 of the double acting piston.

A variety of other alternatives may come to the mind of one skilled in the art in the hemodialysis field. The foregoing alternatives have been briefly described to demonstrate the flexibility of the present invention and to underscore the breadth of the innovative concept forming the basis of the invention.

Thus, the present invention controls the rate of fluid removal from, or addition to, the patient by accurately metering dialysate delivery to and from the hemodialyzer preferably by way of matched pumps. The system of the present invention is based on maintaining relatively constant levels of fresh dialysate and spent dialysate in pre-and postdialyzer receptacles which may be maintained at atmospheric pressure for ease and convenience of operation.

What is claimed is:

1. A method for controlling ultrafiltration during hemodialysis comprising:
   supplying blood to and removing blood from a hemodialyzer;
   supplying fresh dialysate to a dialysate flow path which includes said hemodialyzer, a dialysate reservoir, a first receptacle and a second receptacle, with fresh dialysate being first supplied to said reservoir;
   withdrawing fresh dialysate from said reservoir and delivering same to said first receptacle and then to said hemodialyzer at a controlled flow rate;
   sensing the volume of fresh dialysate in the first receptacle and maintaining same at a relatively constant, pre-determined level;
   withdrawing spent dialysate, including any ultrafiltrate, from said hemodialyzer and delivering same to said second receptacle and then removing same from said second receptacle and out of said dialysate flow path at said controlled flow rate;
   sensing the volume of spent dialysate in the second receptacle and maintaining same at a relatively constant, pre-determined level;
   withdrawing a controlled amount of dialysate from either of said receptacles causing a system response to thereby exert a negative pressure in the dialysate section of said hemodialyzer to effect a withdrawal of ultrafiltrate from the patient's blood into said flow path to substantially balance the amount of dialysate withdrawn therefrom.

2. The method of claim 1 wherein fresh dialysate is supplied to said first receptacle and spent dialysate is removed from said second receptacle by respectively pumping said fresh and said spent dialysate at substantially equivalent fixed rates of flow.

3. The method of claim 2 which further includes calibrating said rates of pumping to assure that they are substantially equivalent during operation.

4. The method of claim 1 which includes maintaining said receptacles at atmospheric pressure during hemodialysis.

5. The method of claim 1 which includes maintaining said receptacles at a pre-selected pressure during hemodialysis.

6. The method of claim 1 wherein said maintaining of fresh dialysate at the pre-determined level and said maintaining of spent dialysate at the pre-determined level are achieved by varying the flow rates at which fresh dialysate is withdrawn from the first receptacle and at which spent dialysate is delivered to said second receptacle in response to changes from said pre-determined levels.

7. The method of claim 1 wherein the volume of spent dialysate in the second receptacle is maintained at a relatively constant, pre-determined level substantially equivalent to said pre-determined level of said fresh dialysate in said first receptacle.

8. A method of hemodialytic ultrafiltration in a device utilizing a continuous loop dialysate flow path having a hemodialyzer, a first receptacle and a second receptacle comprising:
   supplying blood to and removing blood from said hemodialyzer;
   supplying fresh dialysate to said first receptacle and withdrawing spent dialysate from said second receptacle at substantially equivalent rates;
   withdrawing fresh dialysate at variable flow rates from said first receptacle and supplying same to said hemodialyzer;
   withdrawing spent dialysate, including any ultrafiltrate, at variable flow rates from said hemodialyzer and delivering same to said second receptacle;
   maintaining the dialysate levels in said receptacles at relatively constant, pre-determined levels; and
   withdrawing a controlled amount of dialysate from either of said receptacles to thereby effect a withdrawal of ultrafiltrate from the patient's blood into said flow path to substantially balance the amount of dialysate withdrawn therefrom.

9. A method of liquid infusion into a patient utilizing an apparatus with a dialysate flow path comprising a fluid-separation device with a liquid permeable membrane therein, a first receptacle and a second receptacle, said method comprising:
   supplying blood to and removing blood from said device;
   supplying fresh liquid to said first receptacle and withdrawing spent liquid from said second receptacle at substantially equivalent rates;
   withdrawing fresh liquid at variable flow rates from said first receptacle and supplying same to said device;
   withdrawing spent liquid at variable flow rates from said device and delivering same to said second receptacle;
   maintaining the liquid levels in said receptacles at relatively constant, pre-determined levels; and
   supplying a controlled amount of infusate to the fresh liquid upstream of said device to thereby effect an infusion of infusate into the patient's blood from said flow path.

10. An apparatus for controlling ultrafiltration during hemodialysis comprising a dialysate flow path having a fresh dialysate supply line for connection to a source of fresh dialysate and a spent dialysate removal line for connection to drain means, said flow path including, between said supply line and said removal line:
   a hemodialyzer for the dialysis and ultrafiltration of blood including inlet and outlet blood ports, an inlet dialysate port for the entry of fresh dialysate and an outlet dialysate port for the exit of spent dialysate;
   a dialysate reservoir connected to said supply line for the delivery of fresh dialysate thereinto;
   a first receptacle positioned in the flow path between said reservoir and the inlet dialysate port of said hemodialyzer;
   a first controlled flow rate pump for withdrawing fresh dialysate from said reservoir at a controlled rate and delivering same to said first receptacle;
   a first variable rate pump for withdrawing fresh dialysate from said first receptacle at a controlled rate and delivering same to said hemodialyzer;
   first sensing means for sensing the volume of fresh dialysate in said first receptacle and for controlling the flow rate of said first variable pump to maintain the volume of fresh dialysate therein at a relatively constant, pre-determined level;
   a second receptacle positioned in the flow path between said outlet dialysate port of said hemodialyzer and said removal line;
   a second variable rate pump for withdrawing spent dialysate, including any ultrafiltrate from said hemodialyzer at said controlled rate and delivering same to said second receptacle;

second sensing means for sensing the volume of spent dialysate in said second receptacle and for controlling the flow rate of said second variable pump to maintain the volume of spent dialysate therein at a relatively constant, pre-determined level;

a second controlled flow rate pump for withdrawing spent dialysate from said second receptacle at said controlled rate and delivering same to said removal line; and an ultrafiltrate removal pump positioned in the flow path between the output side of said first controlled flow rate pump and the intake side of said second controlled flow rate pump for withdrawing a controlled amount of dialysate from the dialysate flow path between and including of said receptacles to thereby cause said first and second variable rate pumps to respectively change flow rates to seek the equilibrium of said pre-determined levels and exert a zero negative pressure, relative to patient blood pressure, in the dialysate section of said hemodialyzer to effect a withdrawal of ultrafiltrate from the patient's blood into said dialysate flow path to substantially balance the amount of dialysate withdrawn therefrom.

11. The apparatus of claim 10 wherein said ultrafiltrate removal pump is positioned to withdraw a controlled amount of fresh dialysate from said first receptacle.

12. The apparatus of claim 10 wherein said first and second sensing means each includes operative means to further open or restrict the dialysate flow out of said first receptacle and into said second receptacle, respectively, to maintain said pre-determined levels.

13. The apparatus of claim 10 which further includes means for balancing the output of said first controlled flow rate pump with the intake of said second controlled flow rate pump.

14. The apparatus of claim 13 wherein said balancing means includes a shunt line providing a direct fluid flow communication between the output of said first controlled flow rate pump and the intake of said second controlled flow rate pump for calibrating the output of said first controlled flow rate pump with the intake of said second controlled flow rate pump.

15. The apparatus of claim 14 wherein said balancing means further includes a calibration bleed-off line extending between the output side of said first controlled flow rate pump and said reservoir to remove excess dialysate when said first controlled flow rate pump operates at a higher flow rate than said second controlled flow rate pump.

16. The apparatus of claim 13 wherein said balancing means includes restriction means on the output side of said first controlled flow rate pump to restrict the flow of spent dialysate flow therefrom when said first controlled flow rate pump operates at a higher flow rate than said second controlled flow rate pump.

17. The apparatus of claim 10 wherein the first and second receptacles each includes vent means therein so that said receptacles are operable at atmospheric pressure.

18. The apparatus of claim 10 wherein the first and second receptacles are sealed from the atmosphere so that said receptacles are operable at a pre-selected pressure, and said first and said second sensing means sense the pressures, instead of volumes, inside said respective receptacles for controlling said pre-determined levels.

19. The apparatus of claim 10 wherein said reservoir includes an overflow line connected to said removal line, and wherein an air vent is included in said overflow line and in said removal line near the output side of said second controlled flow rate pump to control the pressures influencing the operation of said controlled flow rate pumps.

20. Hemodialysis ultrafiltration apparatus comprising a dialysate flow path including:
a hemodialyzer;
means for supplying blood to and removing blood from said hemodialyzer;
a first receptacle;
a second receptacle;
first means for supplying fresh dialysate to said first receptacle and for withdrawing spent dialysate from said second receptacle at substantially equivalent and fixed rates;
second means for variably withdrawing fresh dialysate from said first receptacle and supplying same to said hemodialyzer and for variably withdrawing spent dialysate, including any ultrafiltrate, from said hemodialyzer and delivering same to said second receptacle;
control means associated with said receptacles and said first and said second means for maintaining the dialysate levels in said receptacles at relatively constant, pre-determined levels; and
ultrafiltrate removal means for withdrawing a controlled amount of dialysate from the dialysate flow path between and including said receptacles to thereby effect a withdrawal of ultrafiltrate from the patient's blood into said flow path to substantially balance the amount of dialysate withdrawn therefrom.

21. Liquid infusion apparatus comprising a liquid flow path including:
a flow-separation device with a liquid permeable membrane therein;
means for supplying blood to and removing blood from said device;
a first receptacle;
a second receptacle;
first means for supplying fresh liquid to said first receptacle and for withdrawing spent liquid from said second receptacle at substantially equivalent and fixed rates;
second means for variably withdrawing fresh liquid from said first receptacle and supplying same to said device and for variably withdrawing spent liquid from said device and delivering same to said second receptacle;
control means associated with said receptacles and said first and said second means for maintaining the liquid levels in said receptacles at relatively constant, pre-determined levels; and
infusate delivery means for supplying a controlled amount of infusate to the fresh liquid upstream of said device to thereby effect an infusion of infusate into the patient's blood from said flow path.

* * * * *